United States Patent [19]

Morohashi et al.

[11] Patent Number: 4,798,457
[45] Date of Patent: Jan. 17, 1989

[54] SELF-CONSCIOUS TYPE EYE EXAMINING APPARATUS

[75] Inventors: Kazuo Morohashi, Tokyo; Nobuyuki Miyake, Yokohama; Tsunemi Gonda, Yamato, all of Japan

[73] Assignee: Nikon Corporation, Tokyo, Japan

[21] Appl. No.: 93,158

[22] Filed: Sep. 1, 1987

Related U.S. Application Data

[63] Continuation of Ser. No. 816,992, Jan. 9, 1986, abandoned, which is a continuation of Ser. No. 526,794, Aug. 26, 1983, abandoned.

[30] Foreign Application Priority Data

Sep. 3, 1982 [JP] Japan .............................. 57-152759

[51] Int. Cl.[4] .............................................. A61B 3/02
[52] U.S. Cl. ..................................... 351/235; 351/234
[58] Field of Search ........................................ 351/233

[56] References Cited

U.S. PATENT DOCUMENTS

| | | | |
|---|---|---|---|
| 3,860,330 | 1/1975 | Persson | 351/235 |
| 3,969,020 | 7/1976 | Lynn et al. | 351/243 |
| 4,185,896 | 1/1980 | Buhler | 351/235 |
| 4,192,582 | 3/1980 | Aoki et al. | 351/235 |
| 4,385,813 | 5/1983 | Klein et al. | 351/235 X |
| 4,496,226 | 1/1985 | Augusto et al. | 351/234 |

OTHER PUBLICATIONS

Duane, Clinical Ophthalmology, vol. 1, Harper & Row; Chapter 38, 1978.

Primary Examiner—Rodney B. Bovernick
Attorney, Agent, or Firm—Shapiro and Shapiro

[57] ABSTRACT

A self-conscious type eye examining apparatus is provided with a Stokes' cross cylinder in a view field window, a spherical lens group having a plurality of spherical lenses selectively disposed in the optical path of the cross cylinder, a first electric rotating device coupled to the cross cylinder to rotate the cross cylinder independently, a second electric rotating device for inserting a predetermined lens of the spherical lens group into the view field window, and a control device for controlling the rotations of the first and second electric rotating devices in a predetermined relation.

5 Claims, 12 Drawing Sheets

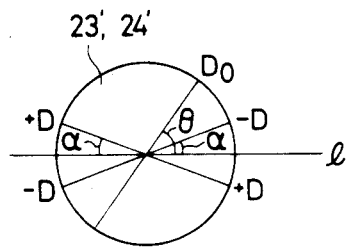

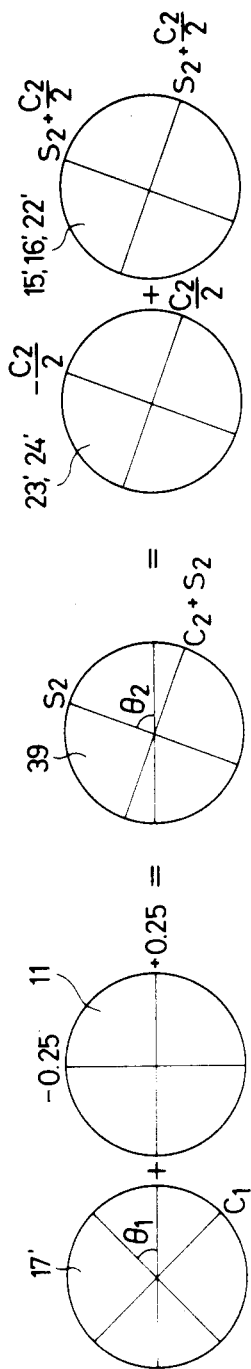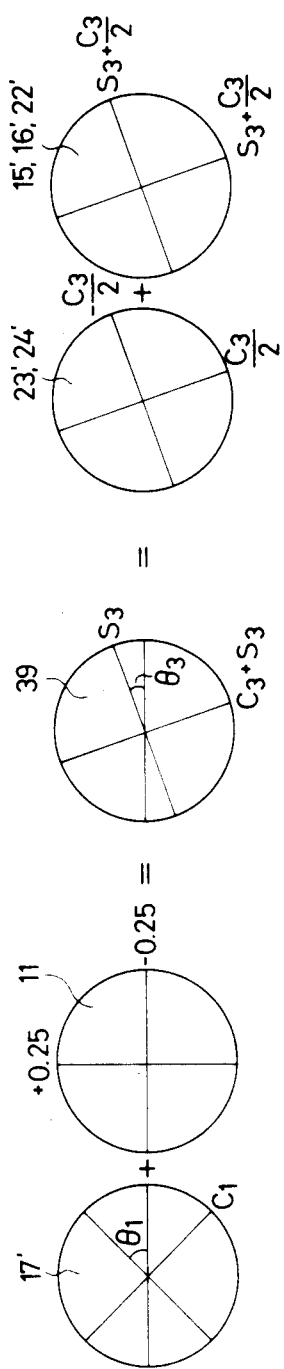
FIG. 12A
FIG. 12B

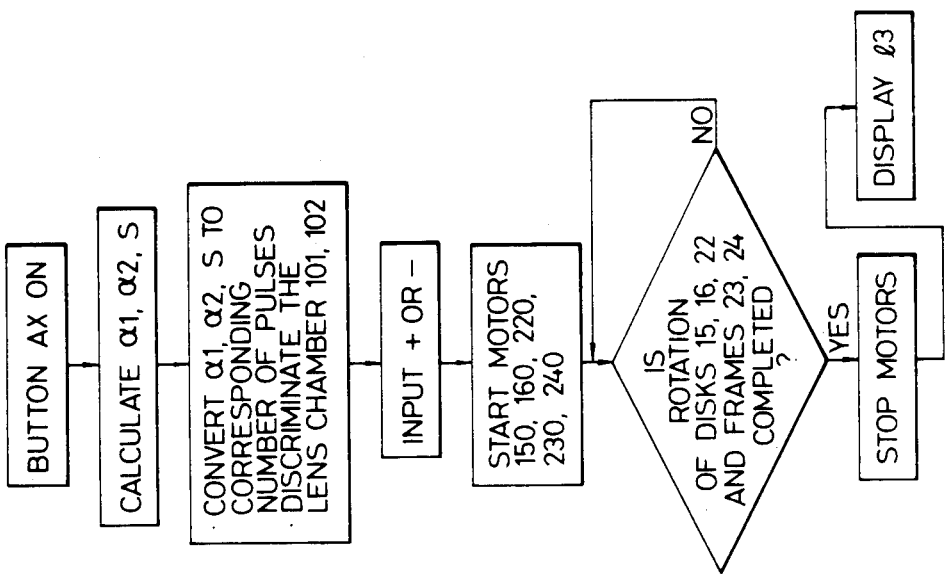
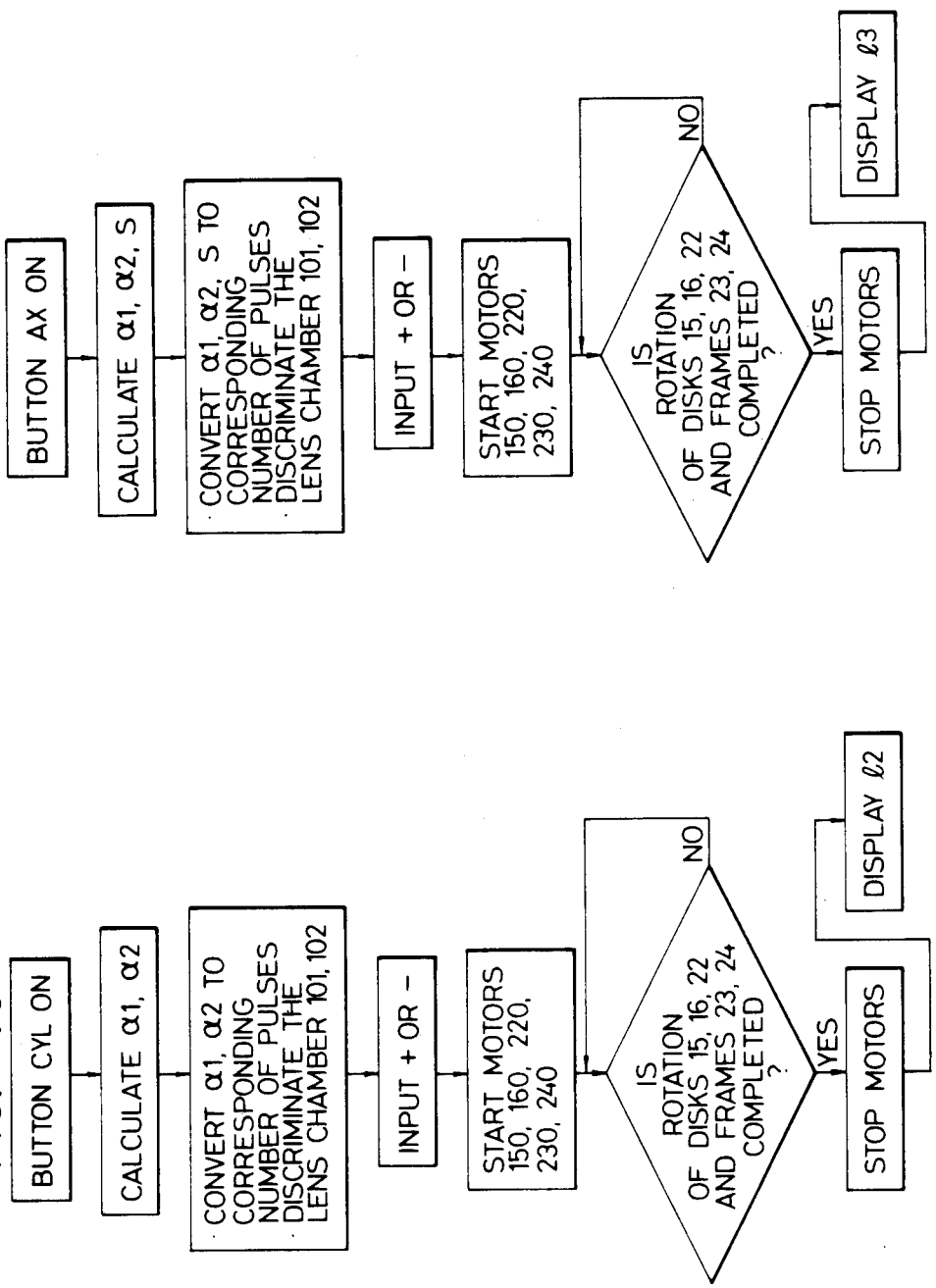

SELF-CONSCIOUS TYPE EYE EXAMINING APPARATUS

This is a continuation application of Ser. No. 816,992 filed Jan. 9, 1986, which is a continuation application of Ser. No. 526,794 filed Aug. 26, 1983, both of which are now abandoned.

BACKGROUND OF THE INVENTION

1. Field of the Invention

This invention relates to a self-conscious type examining apparatus.

2. Description of the Prior Art

The conventional self-conscious type eye examining apparatus used for sight measurement in ophthalmology, as shown in FIG. 1 of the accompanying drawings, is formed substantially symmetrically and set so that the centers of the view field windows 1 of left and right lens chambers R are coincident with the examinee's eyes, and the operator changes lenses within the view field windows 1 and chooses appropriate lenses while asking the examinee looking into a sight chart lying on this side of FIG. 1 through the view field windows 1 as to how the examinee sees the chart. The change of the lenses is accomplished by means of handles 2 to 6. Holding plates for lenses are contained in the lens chambers R and each of the holding plates 14 to 17 is in the form of a disc centered about a shaft 18. The disc 14 holds on the same circumference an opening for releasing the view field, a shield plate for shielding the view field, and optical elements including both-eye examining lenses such as a polarizing lens, a prism lens, etc. and a prism diopter measuring lens such as a Maddox rod. The disc 14 is rotated by the handle 2 and desired optical elements are inserted into the view field windows 1. Chosen optical elements are displayed by display plates 8. Lenses having different refracting characteristics are held by the discs 15 to 17 at equally divided angles about an axis correspondingly to the number of lenses. Eleven different spherical lenses 15' are held on the disc 15 with a spacing of 3D therebetween from −18D to +15D (D indicates diopter). Rotation of the disc 15 may be accomplished by means of the handle 6 through a gear, not shown. Eleven different spherical lenses 16' are held on the disc 16 with a spacing of 0.25D therebetween from −1.00D to +1.75D. Rotation of the disc 16 may be accomplished by means of the handle 5 through a gear, not shown. The spherical powers of the lens chambers R overlap in the view field windows 1 and become the value of the sum of the diopters of the two lenses 15' and 16' and as a result, making lenses of different characteristics appear in the view field windows 1 with a spacing of 0.25D from −19.00D to +16.75D becomes possible. To change the power continuously, it is necessary to rotate the discs 15 and 16 at the same time and therefore, an intermittent mechanism (not shown) such as a Geneva mechanism is generally used between the discs 15 and 16. The powers of the spherical lenses are displayed by display windows 7. Nine different astigmatic lenses are held on the disc 17 with a spacing of 0.25D from 0D to −2.25D, and each of them is contained in a gear 19 rotatable in the disc 17 so that the cylindrical axis thereof is rotatable. The disc 17 fixed to a gear 21 is made rotatable by rotating the gear 21 by means of the handle 4 through a gear, not shown. Cylindrical powers are displayed by display windows 9. As regards rotation of the cylindrical axis, a gear 20 is made rotatable by means of the handle 3 through a gear, not shown, and the gear 20 is coupled to all gears 19 containing cylindrical lenses therein and as a result, rotation of all cylindrical lenses about the axes thereof are made possible by rotation of the handle 3. Cylindrical axes are displayed by display plates 10. In the apparatus of this type, devices 11 called cross cylinders for precisely measuring the cylindrical power and cylindrical axis are provided outside the lens chambers R. The cross cylinders 11 are usually provided outside the view field windows 1 (at the positions shown) and are rotated about the shafts 13 only when required, whereby they are inserted into the view field windows 1 to effect measurement. The cross cylinders 11, as shown in FIGS. 3 and 4 of the accompanying drawings, are cylindrical lenses in which the absolute values of the maximum power and the minimum power are equal to each other and differ in sign and the principal meridan direction indicative of the maximum power is orthogonal to the principal meridian direction indicative of the minimum power, and usually, 0.25D or 0.5D is used as the absolute value (the Figure shows a cross cylinder of 0.25D). As shown in FIG. 3A, the principal meridian (the direction of +0.25D) indicative of the maximum power is adjusted to the cylindircal axis direction B of the examinee, the cross cylinder 11 is reversed by means of a knob 12 (FIG. 3B) and precise measurement of the cylindrical power is effected before and after the reversal by comparing the manners in which the chart is seen by the examinee. Precise measurement of the cylindrical axis is accomplished by adjusting the principal meridian indicative of the maximum power (the direction of +0.25D) to the direction of 45° with respect to the cylindrical axis direction B of the examinee as shown in FIG. 4A (rotating the cross cylinder 11 by 45° relative to FIG. 3B), and then reversing the cross cylinder (FIG. 4B), and comparing the manners in which the chart is seen before and after the reversal. During measurement, when the disc 17 is rotated to interchange the cylindrical lens or the gear 19 is rotated to change the cylindrical axis, it is necessary to again effect the examination by the cross cylinders. For the purpose of facilitating this reexamination, the cross cylinders 11 and the cylindrical axis of the cylindrical lens on the disc 17 are always operatively associated with each other and, when the cylindrical axis is rotated by means of the handle 3, the cross cylinders 11 are likewise rotated.

In this manner, in the conventional cross cylinders 11, the position of the reversing knob 12 during measurement of cylindrical power (FIG. 3) and the position of the reversing knob 12 during measurement of cylindrical axis (FIG. 4) differ from each other by 45° and, when the cross cylinders 11 are rotated to rotate the cylindrical axis, the knob 12 also is rotated together therewith and therefore the position of the knob is not fixed, and this has led to poor operability. Also, the knob 12 must be operated so as not to obstruct the view field of the examinee and this has led to the disadvantage that the examiner is compelled to assume an unnatural posture.

SUMMARY OF THE INVENTION

It is an object of the present invention to overcome the above-noted disadvantages and to provide an improved self-conscious type eye examining apparatus.

To achieve such object, the self-conscious type eye examining apparatus of the present invention is provided with a Stokes' cross cylinder in a view field window, a spherical lens group having a plurality of spherical lenses selectively disposed in the optical path of the cross cylinder, a first electric rotating device coupled to the cross cylinder to rotate the cross cylinder independently, a second electric rotating device for inserting a predetermined lens of the spherical lens group into the view field window, and a control device for controlling the rotations of the first and second electric rotating devices in a predetermined relation.

The invention will become more fully apparent form the following detailed description thereof taken in conjunction with the accompanying drawings.

BRIEF DESCRIPTION OF THE DRAWINGS

FIG. 9 is a principle view showing the manner in which the power $D_0$ obtained with two cylindrical lenses overlapped with each other is produced.

FIG. 10 illustrates the principle for making a cylindrical lens in which the principal meridian is 45° and the cylindrical power is $-2D \sin 2\alpha$.

FIG. 11A illustrates the principle of the precise measurement of cylindrical power.

FIG. 11B shows the cross cylinder of FIG. 11A as reversed.

FIG. 12A illustrates the principle of the precise measurement of cylindrical axis.

FIG. 12B shows the cross cylinder of FIG. 12A as reversed.

FIG. 18 is a flow chart of the operation of precise measurement of cylindrical power by the cross cylinder.

FIG. 19 is a flow chart of the operation of precise measurement of cylindrical axis.

DESCRIPTION OF THE PREFERRED EMBODIMENTS

Figure 1:
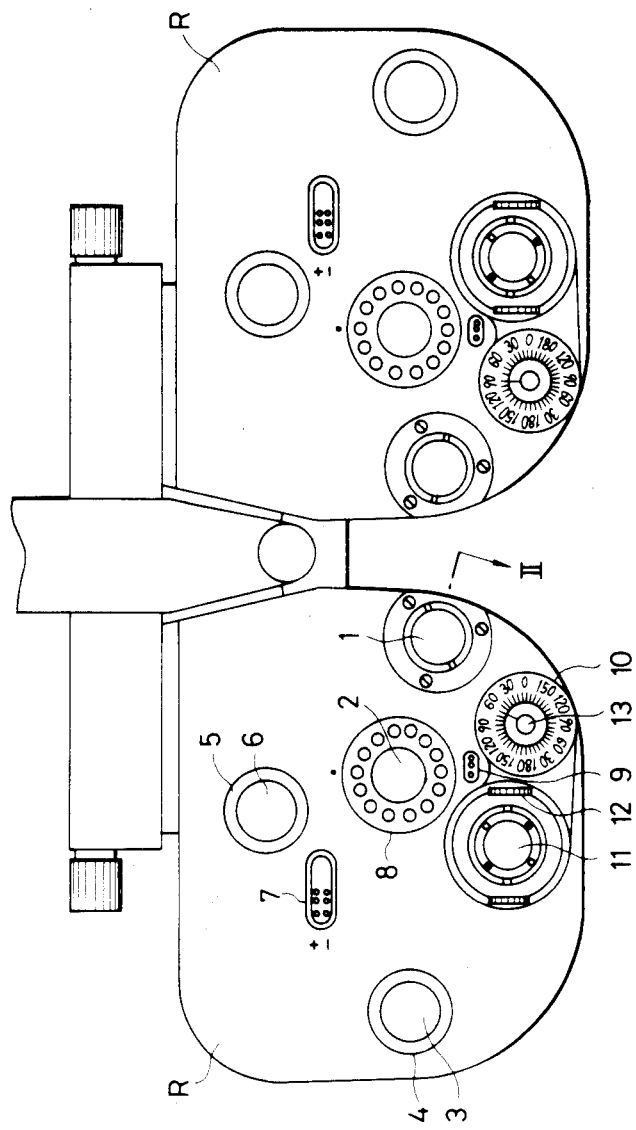
FIG. 1 is a front view of chiefly the lens chambers of a manually operated self-conscious type eye examining apparatus according to the prior art.

The invention will hereinafter be described with respect to an embodiment shown in the drawings.

The lens chambers 101 and 102 of the present embodiment do not have an operating handle but are provided with a large-sized display panel so that the sphere, cylinder and axis of lenses inserted in view field windows 103 and 104 are displayed by display elements such as liquid crystal and thus have a neat appearance. As will later be described, various lenses, etc. are contained in the lens chambers 101 and 102 and these are changed over by rotation of a pulse motor. To control the rotation of a pulse motor, a control device 51 is connected to the lens chambers 101 and 102 through cord 50, and by inputting suitable information to an operating panel 52, a signal for controlling the rotation of the pulse motor is introduced from the control device 51 into the lens chambers. The control device 51 may be a microcomputer.

Figure 2:
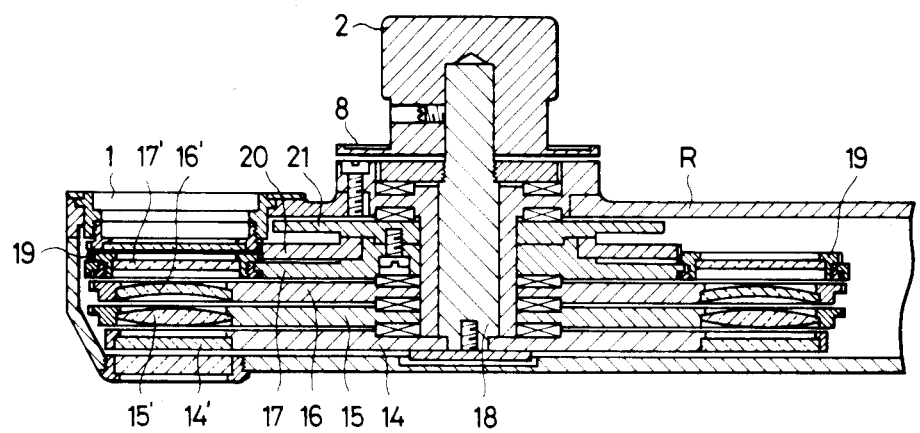
FIG. 2 is a fragmentary cross-sectional view taken along the arrow II of FIG. 1.
Figure 6:
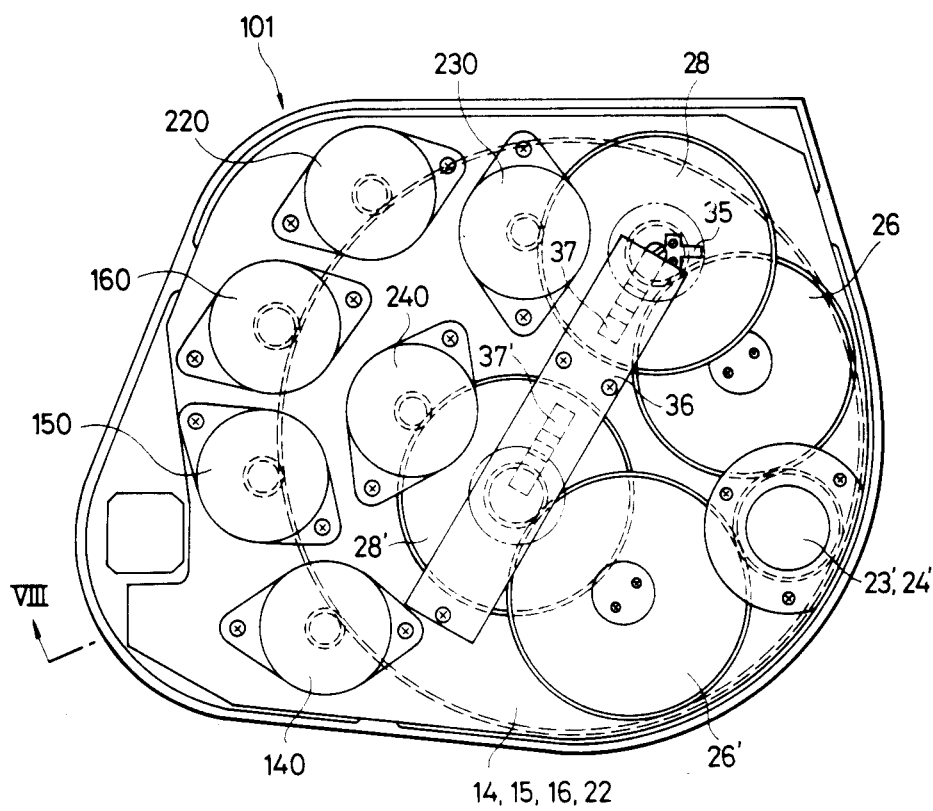
FIG. 6 shows the internal structure of the apparatus of FIG. 5.
Figure 7:
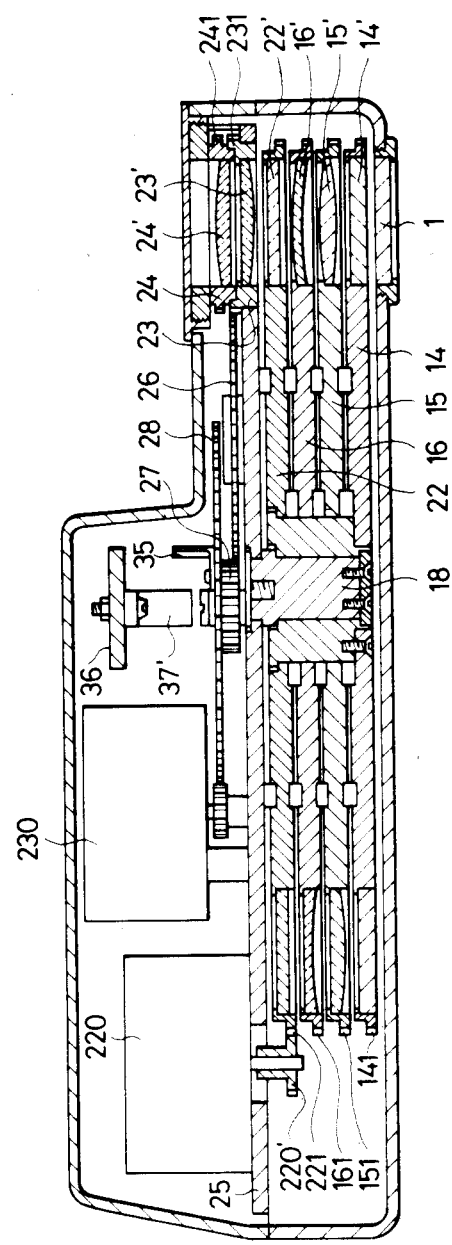
FIG. 7 is a cross-sectional view taken along the line VII—VII of FIG. 5.

Within each of the lens chambers, a disc 14 similar to that of FIG. 2, a disc 15 holding different spherical lenses 15' with a spacing of 3D, and a disc 16 holding different spherical lenses 16' with a spacing of 0.25D are disposed for rotation about a central shaft 18, as shown in FIG. 7. A gear 141 is formed on the outer pheripheral surface of the disc 14, and the gear head of a pulse motor 140 shown in FIG. 6 is in mesh engagement with the gear 141. Gears 151 and 161 are also formed on the outer peripheral surfaces of the discs 15 and 16, respectively, and the gear head of a pulse motor 150 shown in FIG. 6 is in mesh engagement with the gear 151 and the gear head of a pulse motor 160 shown in FIG. 6 is in mesh engagement with the gear 161. A disc 22 is further disposed for rotation about the central shaft 18. The disc 22 is an auxiliary lens plate holding three different spherical lenses 22' of $-0.0625D$, $-0.125D$ and $-0.1875D$, respectively, and formed with an opening, and a gear 221 is formed on the outer periphery of the disc 22, and the gear head 220' of a pulse motor 220 is in mesh engagement with the gear 221. Two cylindrical lenses 23' and 24' having powers equal in absolute value and different in sign are provided to be superposed on a view field window 103. The cylindrical lens 23' is fixed to a frame 23 rotatably held on a fixed base plate 25, and the cylindrical lens 24' is fixed to a frame 24 rotatably held on the frame 23. These two cylindrical lenses 23' and 24' together constitute a so-called Stokes' cross cylinder. Rotation of the frame 23 is accomplished by a pulse motor 230 through a large gear 26 in mesh engagement with a gear 231 formed on the outer peripheral surface of the frame 23, a transmission gear 27 in mesh engagement with the large gear 26, a large gear 28 coaxial with the transmission gear 27, and the gear head of the pulse motor 230 which i in mesh engagement with the large gear 28. Rotation of the frame 24 is also accomplished by a pulse motor 240 through large gears 26', 28' etc. (see FIG. 6).

Figure 8A:
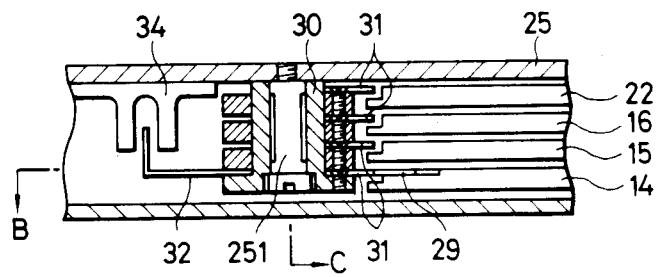
FIG. 8A is a fragmentary cross-sectional view taken along the arrow VIII of FIG. 6.
Figure 8B:
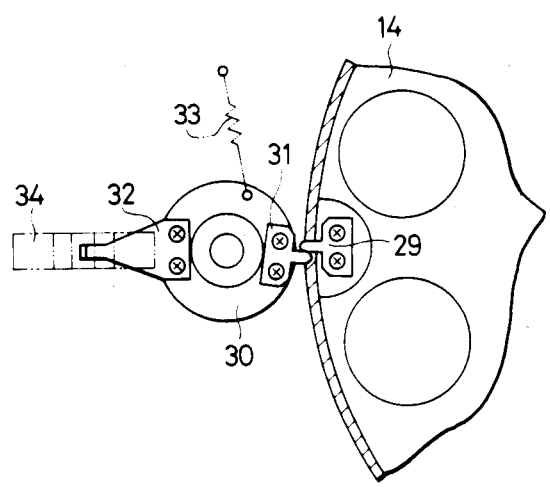
FIG. 8B is a fragmentary cross-sectional view taken along the arrow B of FIG. 8A.
Figure 8C:
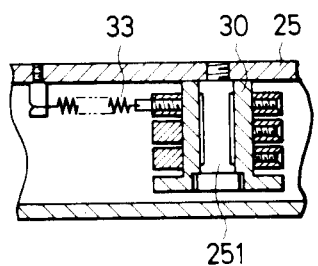
FIG. 8C is a cross-sectional view taken along the arrow C of FIG. 8A.

The setting of the initial positions of the discs 14, 15, 16 and 22 is accomplished by a photoelectric detector device, as shown in FIG. 8. That is, a pawl 29 is fixed to each disc correspondingly to the initial position thereof, while a rotatable member 30 is rotatably disposed about a shaft 251 provided on the fixed base plate 25. The rotatable member 30 is provided with four engaging pawls 31 at such positions whereat the pawls 31 are engaged with the pawls 29 of the discs 14, 15, 16 and 22, and is provided with a light-intercepting plate 32 on the opposite side, and is biased into a stand-by position by a spring 33 having one end thereof secured to the base plate 25. When the pawls 29 become engaged with the pawls 31 to rotate the rotatable member 30 against the force of the spring 33, the light-intercepting plate 32 intercepts the optical path of a photocoupler 34 and operates so that an initial position signal is obtained from the photocoupler 34. After the initial position signal has been obtained, each of the discs 14, 15, 16 and 22 is rotated by a predetermined sufficient amount so that the light-intercepting plate 32 retracts from the photocoupler, and this position is the initial position of each of the discs 14, 15, 16 and 22.

A photoelectric detector device is provided to set the initial position during the rotation of the frames 23 and 24 as well. That is, as shown in FIG. 6, a light-intercepting plate 35 fixed to large gears 28 and 28' (only that side which is adjacent to the large gear 28 is shown and as regards that side which is adjacent to the large gear 28', only the locus of the fore end is shown in dot-and-dash line) intercepts the optical paths of photocouplers 37 and 37' fixed to a mounting plate 36, whereby initial position signals are obtained from the photocouplers 37 and 37'.

The cylinder and axis may be found by the Stokes' cross cylinder on the basis of the following principle.

It is known that when, as shown in FIG. 9, the power of the cylindrical lens 23' is $-D$ and the axis thereof is inclined by an angle $\alpha$ with respect to a reference direction 1 while the power of the cylindrical lens 24' is $+D$ and the axis thereof is inclined by an angle $\pi - \alpha$ with respect to the reference direction 1, in the Stokes' cross cylinder obtained by superposing these two cylindrical lenses 23' and 24' one upon the other, the power $D_0$ in the angle $\theta$ direction (hereinafter referred to as the axis $\theta$) relative to the reference direction 1 is expressed as $$D_0 = -D\cos^2(\theta - \alpha) + D\cos^2(\theta + \alpha) = [(-D)\sin 2\alpha]\sin 2\theta \quad (1)$$

According to equation (1), it is seen that when the axis $\theta$ is at 45°, the power $D_0$ assumes a maximum value $-D \sin 2\alpha$ and when the axis $\theta$ is at 135°, the power $D_0$ assumes a maximum value $+D \sin 2\alpha$. Thus, there is obtained a cross cylinder having principal meridians in the directions of 45° and 135° with respect to the reference direction and having a cylindrical power of $\pm D \sin 2\alpha$. When a spherical lens formed by spherical lenses 15', 16' and 22' and having a spherical power of $-D \sin 2\alpha$ is superposed on the above-described Stokes' cross cylinder, a cylindrical lens having a principal meridian of 45° with respect to the reference direction and a cylindrical power of $-2D \sin 2\alpha$ can be made. In FIG. 10, the left side of the sign of equality shows that the Stokes' cross cylinders 23' and 24' have been superposed on the spherical lenses 15', 16' and 22' and the right side of the sign of equality shows the lens obtained as the result thereof. In the above-described embodiment, to change the cylindrical power substantially at an interval of 0.125D, the design is such that the cylindrical power of the two cylindrical lenses 23' and 24' is 3D and the angle $\alpha$ is moved at an interval of 0.5° and that the spherical lens 22' of the auxiliary lens plate 22 is suitably selected and superposed on the spherical lenses 15' and 16' of other holding plates 15 and 16, respectively.

For example, to make a cylindrical lens in which the power is $C_1(= \sin 2\alpha)D$ and the direction of the axis is $\theta_1$, a cross cylinder having a cylindrical power of $\pm(C_1/2)D$ formed by two cylindrical lenses 23' and 24' may be made by changing the angle $\alpha$, a spherical lens having a spherical power $(C_1/2)D$ may be made by a combination of three spherical lenses 15', 16' and 22', and the two cylindrical lenses 23' and 24' may be rotated in the same direction by the same angle $\beta$ so that the direction of axis of the cross cylinder is $\theta_1$. In the above-described combination of the lenses, the cylindrical power cannot be varied exactly at an interval of 0.125D, whereas this offers no problem in practice.

Figures 3A, 3B:
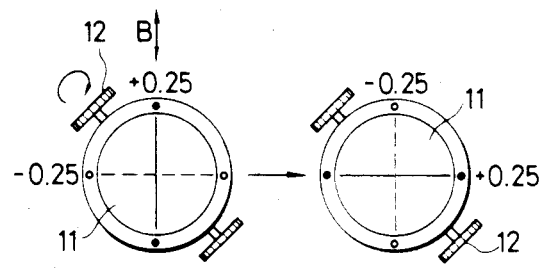
FIGS. 3A and 3B show the state of the precise measurement of cylindrical power by the conventional cross cylinder.
Figures 4A, 4B:
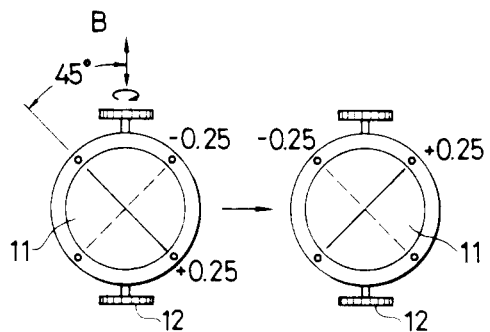
FIGS. 4A and 4B show the state of the precise measurement of cylindrical axis by the conventional cross cylinder.
Figure 5:
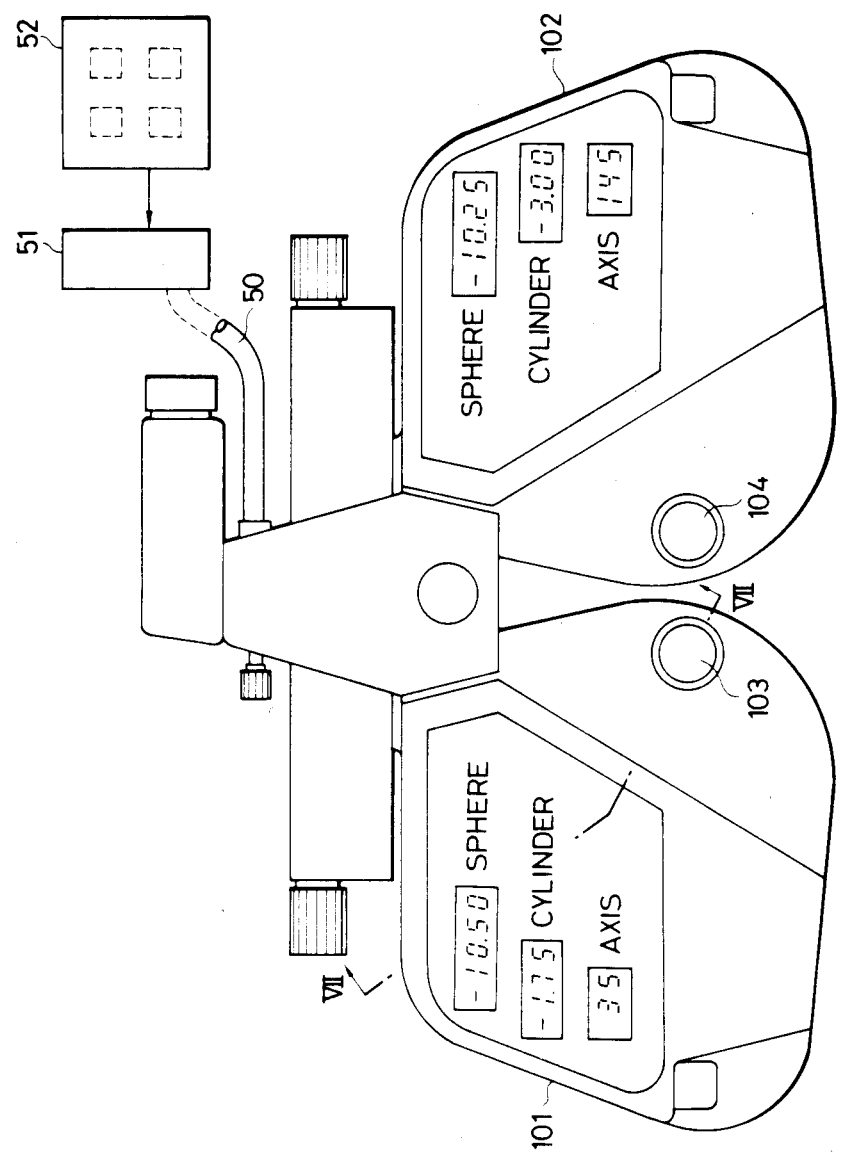
FIG. 5 shows the appearance of an apparatus according to an .embodiment of the present invention.

To effect precise measurement of cylindrical power (corresponding to FIG. 3) and precise measurement of cylindrical axis (corresponding to FIG. 4) by the use of the two cylindrical lenses 23' and 24', a case where a cylindrical lens in which the power is $C_1D$ and the direction of the axis is $\theta_1°$ is in the view field window 1 is considered.

[Precise Measurement of Cylindrical Power]

In FIGS. 11A and 11B, the left side of the sign of equality shows the condition in the case of the conventional precise measurement of cylindrical power, and FIG. 11B corresponds to a condition in which the cross cylinder 11 has been reversed in FIG. 11A. The right side of FIGS. 11A and 11B shows a combination two cylindrical lenses 23' and 24' and spherical lens which is equivalent to the left side. This shows that the precise measurement of cylindrical power heretofore accomplished by an astigmatic lens and cross cylinder can be realized by a Stokes' cross cylinder and a spherical lens superposed one upon the other. As previously described, the power $C_1D$ is equal to (3 sin $2\alpha$)D and therefore, the angle $\alpha$ is first varied to make a cylindrical power $\pm((C_1/2) + 0.25)D$ (FIG. 11A) by an angle $\alpha_1$ and then make a cylindrical power $\pm((C_12) + 0.25)D$ (FIG. 11B) by an angle $\alpha_2$. Thus, the same action as that provided by superposing a cross cylinder having a cylindrical power of $\pm 0.25D$ on a cylindrical lens in which the power is $C_1D$ and the axis is $\theta_1$ and reversing the cross cylinder can be provided. Movement from the cylindrical power of $\pm((C_1/2) + 0.25)D$ to the cylindrical power of $\pm((C_1/2) - 0.25)D$ is accomplished by rotating the frames 23 and 24 by pulse motors 230 and 240.

[Precise Measurement of Cylindrical Axis]

A conventional cross cylinder 11 and a cylindrical lens 17' having a power of $C_1$ are shown in the left side of FIGS. 12A and 12B, and two cylindrical lenses 23', 24' and cylindrical lenses 15', 16', 22' are shown in the right side of FIGS. 12A and 12B, and these two sides are optically entirely equivalent to each other as combined with the middle astigmatic lens 39 by the signs of equality. FIG. 12B shows a condition in which the cross cylinder 11 has been reversed in FIG. 12A.

Considering the condition as shown in FIG. 12A before the cross cylinder 11 is reversed, the composite lens system comprising three cylindrical lenses in which the powers are $C_1D$, $+0.25D$ and $-0.25D$, respectively, can be replaced by a lens 39 in which the spherical power is $S_2$, the cylindrical power is $C_2$ and the axis direction $\theta_2$. That is, $$2\theta_2 = \tan^{-1}\frac{0.25\sin2(\theta_1 - 45) + C_1\sin2\theta_1 - 0.25\sin2(\theta_1 + 45)}{0.25\cos2(\theta_1 - 45) + C_1\cos2\theta_1 - 0.25\cos2(\theta_1 + 45)}$$

$$= \tan^{-1} \frac{-0.5 \cdot \cos 2\theta_1 + C_1 \sin 2\theta_1}{0.5 \cdot \sin 2\theta_1 + C_1 \cos 2\theta_1}$$

$$C_2 = \frac{0.25 \sin 2(\theta_1 - 45) + C_1 \sin 2\theta_1 - 0.25 \sin 2(\theta_1 + 45)}{\sin 2\theta_2}$$

$$= \frac{-0.5 \cdot \cos 2\theta_1 + C_1 \cdot \sin 2\theta_1}{\sin 2\theta_2}$$

$$S_2 = \frac{(0.25 - C_2) + (C_1 - C_2) + (-0.25 - C_2)}{2}$$

$$= \frac{C_1 - 3C_2}{2}.$$

On the other hand, such a lens in which the spherical power is $S_2$, the cylindrical power is $C_2$ and the axis direction is $\theta_2$ can be decomposed into cross cylinders 23', 24' having a cylindrical power of $\pm(C_2/2)$D and spherical lenses 15', 16' and 22' having a spherical power of $(S_2 + (C_2/2))$D. To obtain the axis direction $\theta_2$, the two cylindrical lenses 23' and 24' may be rotated together.

Also, considering the condition as shown to FIG. 12B after the cross cylinder 11 has been reversed, the composite lens system comprising three cylindrical lenses in which the powers are $C_1$D, +0.25D and −0.25D, respectively, can be replaced by a lens 40 in which the spherical power is $S_3$, the cylindrical power is $C_3$ and the axis direction is $\theta_3$. That is, $$S_3 = \frac{C_1 - 3C_3}{2}$$

$$C_3 = \frac{0.5 \cdot \cos 2\theta_1 + C_1 \cdot \sin 2\theta_1}{\sin 2\theta_3}$$

$$2\theta_3 = \tan^{-1}\left(\frac{0.5 \cdot \cos 2\theta_1 + C_1 \cdot \sin 2\theta_1}{-0.5 \cdot \sin 2\theta_1 + C_1 \cdot \cos 2\theta_1}\right)$$

and thus, it is possible to make the composite lens system from a combination of cross cylinders 23', 24' in which the cylindrical power is $\pm(C_3/2)$D and the axis direction is $\theta_3$ and spherical lenses 15', 16', 22' in which the spherical power is $(S_3 + (C_3/22))$D.

Figure 13:
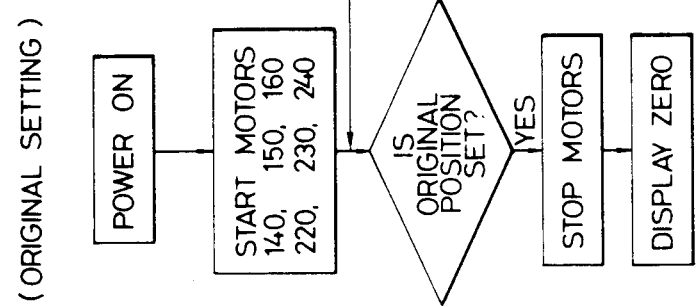
FIG. 13 is a flow chart of the initial setting operation.
Figure 17:
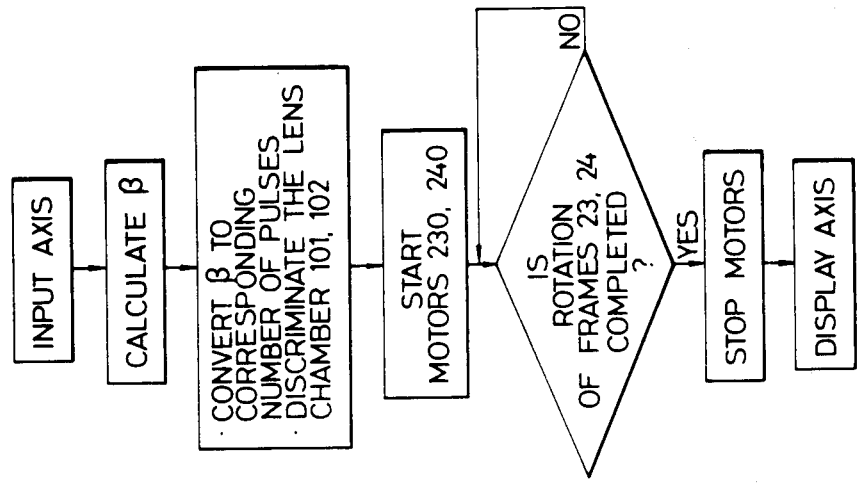
FIG. 17 is a flow chart of the operation of setting cylindrical axis.
Figure 16:
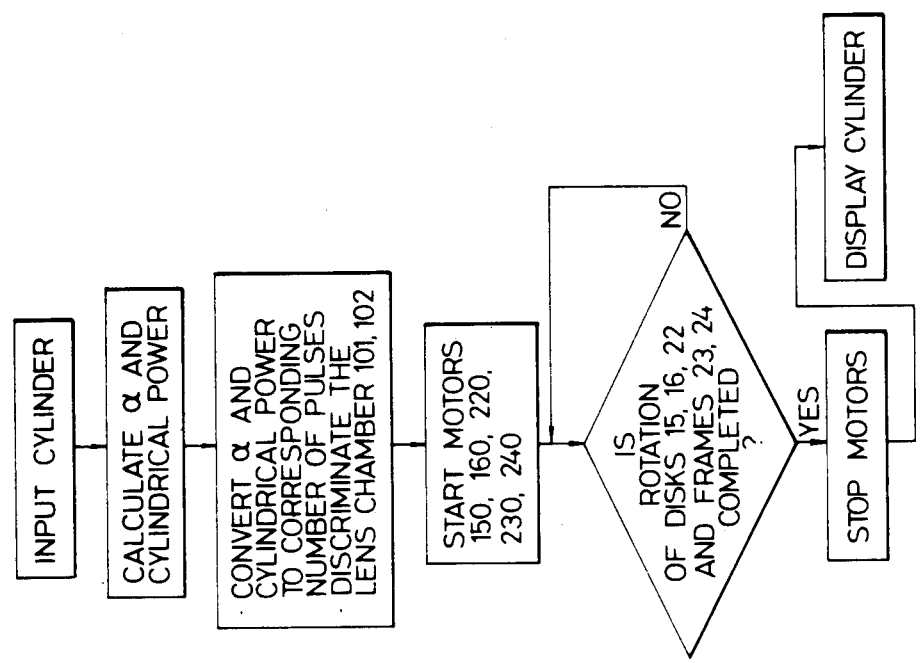
FIG. 16 is a flow chart of the operation of setting cylindrical power.
Figure 20:
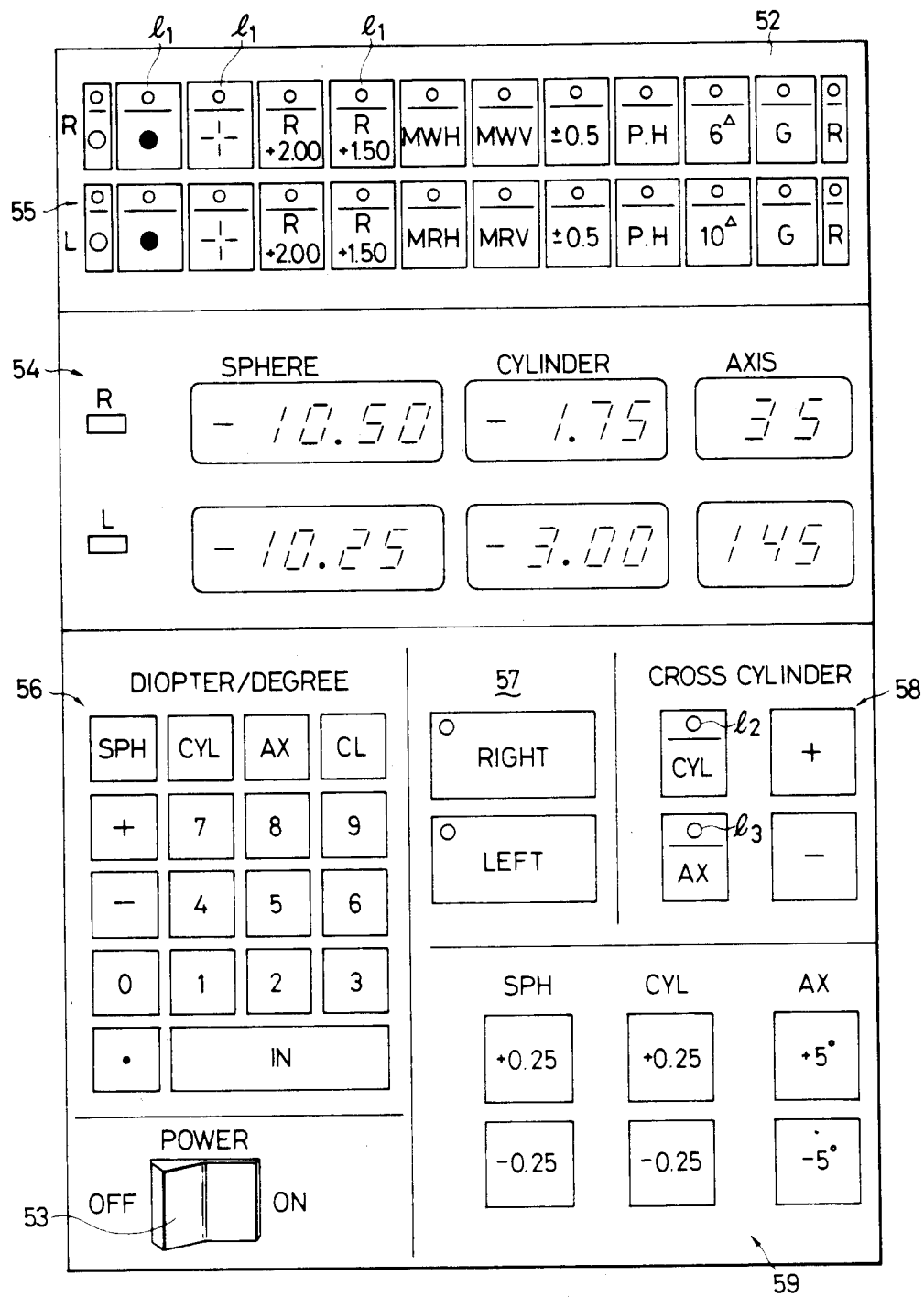
FIG. 20 is a plan view of an operating panel.

Operation will now be described on the basis of flow charts shown in FIGS. 13-19 and the keyboard of an operating panel 52 shown in FIG. 20. When the main switch 53 of the operating panel 52 is closed, a control device 51 starts to operate as shown in FIG. 13. The control device 51 revolves the pulse motors 140, 150, 60, 220, 230 and 240, effects the initial setting of the discs 14, 15, 16, 22 and the two cylindrical lenses 23', 24' and stands by. At this time, the display on the display window 54 of the operating panel 52 and the display on the display panels of the left and right lens chambers 101 and 102 are all zero display.

Figure 14:
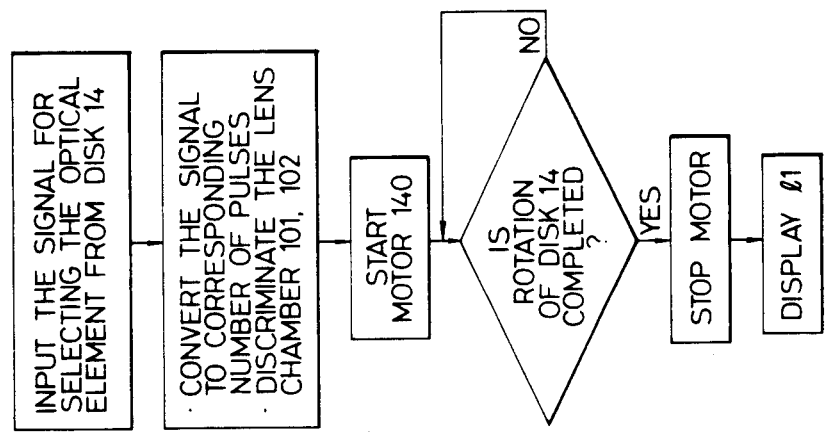
FIG. 14 is a flow chart of the operation of selecting the optical element of a disc 14.

A pair of push button groups 55 operable to set one of the optical elements of the disc 14 in the view field windows 103 and 104 of the lens chambers 101 and 102 are provided on the operating panel 52. When one of the button groups 55 is depressed, the control device 51, as shown in FIG. 14, finds the corresponding number of pulses, and then discriminates the left and right lens chambers and inputs the pulses of the found pulse number to the pulse motor 140 in the designated lens chamber. The pulse motor 140 rotates the disc 14 by the number of pulses input. As a result, a designated optical element is inserted into the view field window. When the supply of the pulses is terminated, the control device 51 inputs a setting completion signal to the display panel 52. As a result, the display lamp $l_1$ of the depressed button is turned on to display that the setting has been completed.

Figure 15:
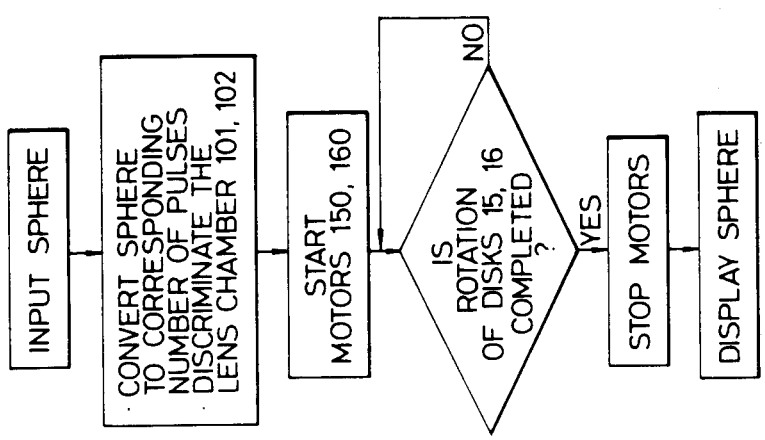
FIG. 15 is a flow chart of the operation of setting spherical power.

Buttons of the button group 56 of the operating panel 52 are operated to set spherical power (SPH), cylindrical power (CYL) and axis direction (AX), and a pair of buttons 57 designate buttons for the right eye (RIGHT) or the left eye (LEFT). Accordingly, to set a spherical power −10.50D to the right eye, the button RIGHT may be depressed, whereafter the button SPH may be depressed and −10.50 may be input by a sign button and a numeric key and the button IN may be depressed, whereby as shown in FIG. 15, the control device 51 converts −10.50 into a number of pulses, discriminates the left and right lens chambers and causes the pulses of the found pulse number to be input to the pulse motors 150 and 160 of the designated lens chamber. The pulse motors 150 and 160 rotate the lens holding plates 15 and 16 by the number of pulses input. As a result, a lens having the designated spherical power is inserted into the view field window. When the supply of the pulses is terminated, the control device 51 inputs a setting completion signal to the operating panel 52. As a result, −10.50 is displayed in the Sphere display window above the display window 54.

To set a cylindrical power −1.75D to the right eye, the buttons RIGHT and CYL are depressed and −1.75 is input by the sign button and the numeric key, whereafter the button IN is depressed. In accordance with FIG. 16, the control device 51 calculates the angle $\alpha$ of such two cylindrical lenses in which the Stokes' cross cylinder is $\pm(1.75/2)$D and the spherical power corresponding to $-(1.75/2)$D, finds the number of pulses imparted to the pulse motors 230 and 240 to achieve the angle $\alpha$ and the number of pulses imparted to the pulse motors 150, 160 and 220 to make the calculated spherical power by the spherical lenses 15', 16' and 22', discriminates the left and right lens chambers, and causes pulses of the found pulse number to be input to the pulse motors 150, 160, 220, 230 and 240 of the designated lens chamber. The pulse motors 150, 160, 220, 230 and 240 rotate the discs 15, 16, 22 and the frames 23, 24 by the number of pulses input. As a result, a lens of the designated cylindrical power is inserted into the view field window. When the supply of the pulses is terminated, the control device 51 inputs a setting completion signal to the operating panel 52 and therefore, −1.75 is displayed in the cylinder display window above the display window 54.

Next, when it is desired that the set axis of the astigmatic lens as described above be set to 35°, the button RIGHT is depressed, the button AX of the button group is depressed and 30 is input by the numeric key, whereafter the button IN is depressed. In accordance with FIG. 17, the control device 51 calculates the angle of rotation $\beta$ of the cross cylinder, finds the number of pulses imparted to the pulse motors 230 and 240, discriminates the left and right lens chambers and causes pulses of the found pulse number to be input to the pulse motors 230 and 240 of the designated lens chamber. The pulse motors 230 and 240 rotate the frames 23 and 24 by the number of pulses input. At this time, the directions and amounts of rotation of the frames 23 and 24 are identical. As a result, the axis direction in the view-field window is set to 35°. When the supply of the pulses is terminated, the control device 51 inputs a setting completion signal to the operating panel 52 and therefore, 30 is displayed in the axis display window above the display window 54.

In this manner, a spherical lens of a desired spherical power and an astigmatic lens of a desired cylindrical power and a desired axis direction can be set.

Cross cylinder examinations may be accomplished by means of four buttons 58 in the portion on the opening panel 52 which is depicted as CROSS CYLINDER. That is, when it is desired to effect precise measurement of cylindrical power, a button CYL is depressed. If this is done, the control device 51, in accordance with FIG. 18, calculates angles $\alpha_1$ and $\alpha_2$, converts them into a number of pulses, discriminates the left and right lens chambers and stands by until one of the sign buttons (+, −) of the four buttons 58 is depressed. The sign buttons (+, −) are for selecting one of the above-mentioned angles $\alpha_1$ and $\alpha_2$. When one of the sign buttons is depressed, the pulse motors 150, 160, 220, 230 and 240 are driven and, when the setting is completed, a setting completion input signal is input to the operating panel 52, so that the display lamp $l_2$ of the button CYL is turned on.

When it is desired to effect precise measurement of cylindrical axis, a button AX is depressed. If this is done, the control device 51, in accordance with FIG. 19, calculates angles $\alpha_1$ and $\alpha_2$ and spherical power S and converts them into a number of pulse. Thereafter, as in the case of the precise measurement of cylindrical power, control of the pulse motors and control of the display of a display lamp $l_3$ are effected.

A button group 59 is further provided on the operating panel 52. This button group 59 is for varying spherical power SPH, cylindrical power CYL and axis direction AX fractionally in the unit as displayed in each button, and the lens in the lens chamber set by a pair of buttons 57 is changed. Of course, along therewith, the display of the display window 54 varies. The buttons CYL and AX of the button group 59 are used so that after the examinee has indicated one of plus (+) and minus (−) which is easier to see by precise examination of cylindrical power and cylindrical axis direction, the button of that sign may be depressed (for example, when the examinee indicates during precise measurement of cylindrical power that plus (+) is easier to see, +0.25 of the button CYL is depressed).

We claim:
1. An eye examining apparatus comprising:
 a base plate having a view field window on an observation optical axis of an eye to be examined;
 a cross cylinder member at a position opposite to said view field window and including a series arrangement of a first cylindrical lens and a second cylindrical lens, the first and second cylindrical lenses having powers with equal absolute values and with different polarities and each of the two cylindrical lenses being rotatable about said observation optical axis;
 a spherical lens member having power of $C_1/2$ at a position opposed to said view field window;
 instruction means for producing first and second instructions alternately, said first instruction designating the creation of cylindrical powers of $C_1+C$ and $-C$ on first and second mutually perpendicular axes, respectively, and said second instruction designating the creation of cylindrical powers of $C_1-C$ and $C$ on said first and second axes, respectively, each of said first and second axes being perpendicular to said observation optical axis; and
 actuating means for producing a relative rotation between said first and second cylindrical lenses in response to said instruction means, said actuating means arranging said first and second cylindrical lenses to a first positional relation in response to said first instruction to create, by a combination of said first and second cylindrical lenses, cylindrical powers of $+((C_1/2)+C)$ and $-((C_1/2)+C)$ on said first and second axes, respectively, and arranging said first and second cylindrical lenses to a second positional relation in response to said second instruction to create, by a combination of said first and second cylindrical lenses, cylindrical powers of $+((C_1/2)-C)$ and $-((C_1/2)-C)$ on said first and second axes, respectively, where c is a constant.

2. An eye examining apparatus according to claim 1, wherein said actuating means actuates said cross cylinder member in response to said first instruction so that a first predetermined angle is formed between a cylindrical axis of said first cylindrical lens and a cylindrical axis of said second cylindrical lens, and actuates said cross cylinder member in response to said second instruction so that a second predetermined angle is formed between the cylindrical axis of said first cylindrical lens and the cylindrical axis of said second cylindrical lens.

3. An eye examining apparatus according to claim 1, wherein said spherical lens member includes plural spherical lens elements arranged in series on said observation optical axis.

4. An eye examining apparatus according to claim 1, further including means for changing the power of said spherical lens member.

5. An eye examining apparatus according to claim 4, wherein said changing means includes plural spherical lens members having mutually different powers and means for replacing said spherical lens having the power of $C_1/2$ at a position opposed to said view field window with one of said plural spherical lens members.

* * * * *